United States Patent [19]
Gorsuch

[11] Patent Number: 5,954,631
[45] Date of Patent: Sep. 21, 1999

[54] DEVICE AND METHOD FOR CREATING AND MAINTAINING A RIGID ERECTION OF A PENIS

[76] Inventor: Leslie L. Gorsuch, 2210 E. B St., Torrington, Wyo. 82240

[21] Appl. No.: 08/936,810

[22] Filed: Sep. 24, 1997

[51] Int. Cl.⁶ .................................................. A61F 5/00
[52] U.S. Cl. ........................................... 600/41; 606/201
[58] Field of Search ................. 600/38–41; 606/201, 606/203

[56] References Cited

U.S. PATENT DOCUMENTS

| | | | |
|---|---|---|---|
| 2,581,114 | 1/1952 | Larson | 600/41 |
| 3,461,863 | 8/1969 | Sullinger | 600/41 |
| 5,085,209 | 2/1992 | Gottschalk | 600/41 |
| 5,221,251 | 6/1993 | Edminster | 600/41 |

FOREIGN PATENT DOCUMENTS 0712163  7/1954  United Kingdom ................... 600/41

*Primary Examiner*—John P. Lacyk
*Attorney, Agent, or Firm*—Shlesinger, Arkwright & Garvey LLP

[57] ABSTRACT

A device for creating and maintaining a rigid erection of a penis comprising a body having a substantially non-contracting width and being adapted for disposition around the penis and first and second terminals attached to the body and being adapted for wrapping around the penis and interlocking with each other; and a method of creating and sustaining a penile erection comprising the steps of supplying a body having a substantially non-contracting width and terminals, placing the body around the penis, wrapping the terminals around the penis, and interconnecting the terminals tight enough so as to prevent blood from exiting the penis.

23 Claims, 4 Drawing Sheets

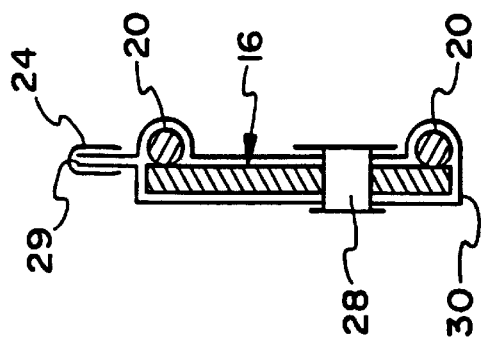
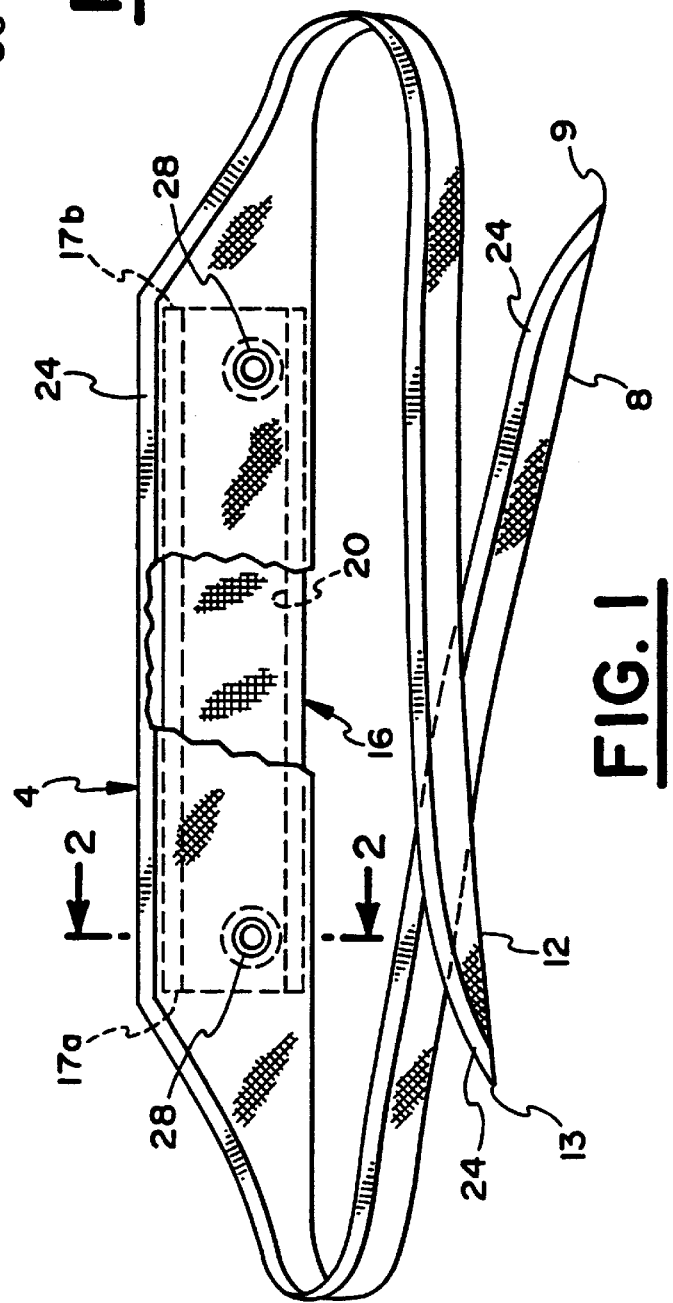

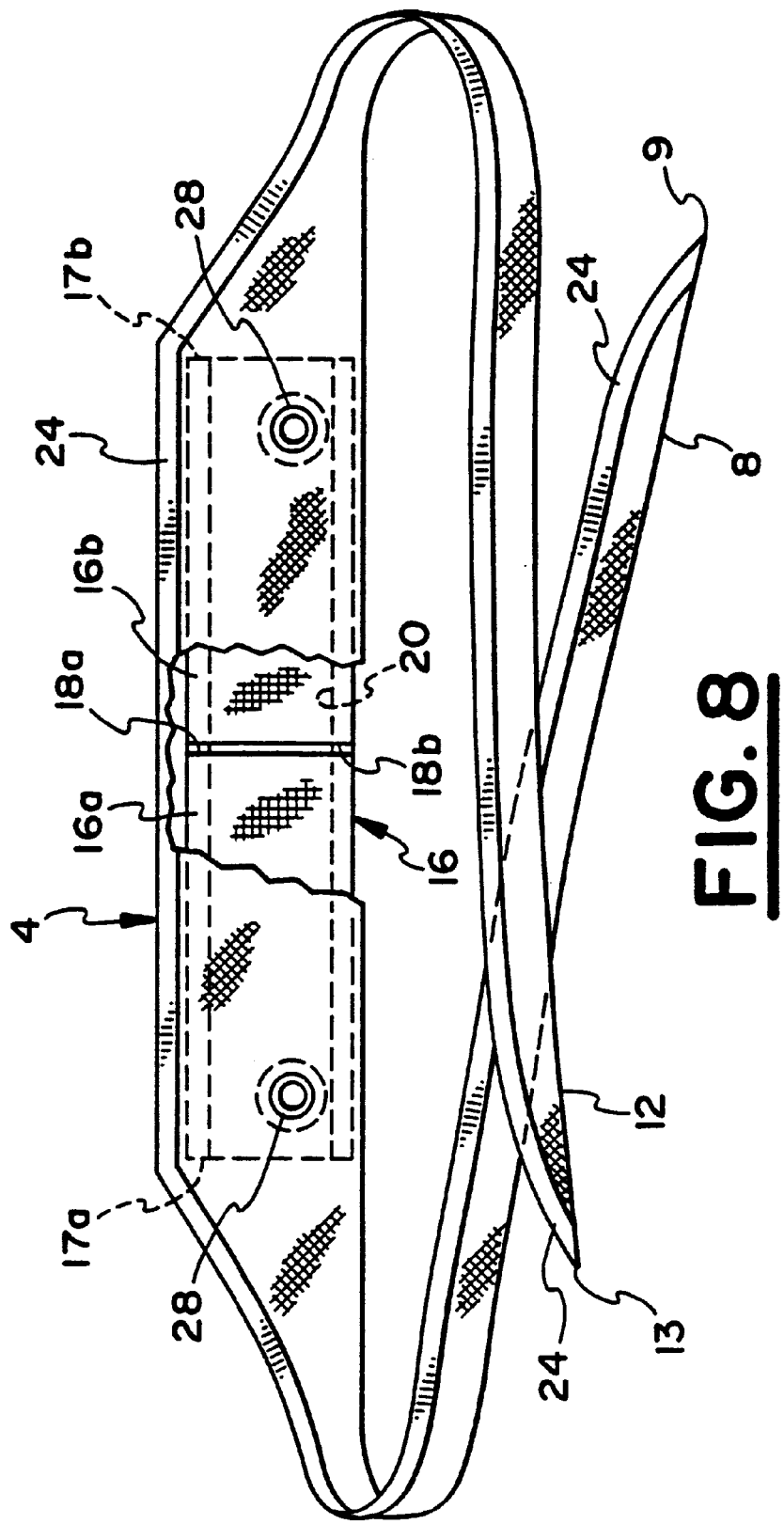

DEVICE AND METHOD FOR CREATING AND MAINTAINING A RIGID ERECTION OF A PENIS

FIELD OF THE INVENTION

This invention relates generally to creating and maintaining an erection of a penis and more particularly to a device that encircles the penis, that is adjustable by the user, and that creates and maintains an erection of a penis.

BACKGROUND OF THE INVENTION

Erectile dysfunction, commonly referred to as impotence, is a condition that effects men of all ages. Erectile dysfunction increases with age. It can hinder a man's sexual activities, diminish self-esteem, and disrupt personal relationships.

Over the years, numerous devices have been developed in an attempt to help men with erectile dysfunction. Examples of some of these devices can be found in: U.S. Pat. No. 3,845,760 granted to Birman, U.S. Pat. No. 1,608,806 granted to Nelson, U.S. Pat. No. 3,926,184 granted to Gehl, U.S. Pat. No. 3,705,580 granted to Gauthier, U.S. Pat. No. 5,221,251 granted to Administer, U.S. Pat. No. 5,338,288 granted to Finkle, U.S. Pat. No. 5,085,209 granted to Gottschalk, and U.S. Pat. No. 4,961,419 granted to Tribble et al.

The known devices have numerous drawbacks such as requiring a cumbersome vacuum pump and/or rubber rings which painfully seize themselves around the penis after engorgement. Rubber rings also may entangle in and pull on pubic hair and often pinch tender skin. Additionally, many of the known devices are quite painful to remove.

According to a recent article in the *Journal of the American Medical Association* dated Jan. 1, 1997 —volume 277 no. 1, The American Urological Association has released new guidelines for the treatment of what they describe as an "organic erectile dysfunction". *The New England Journal of Medicine* on Jan. 2, 1997, published an article entitled "Treatment Of Men With Erectile Dysfunction With Transurethral Alprostadil". These two articles mention the current treatments for erectile dysfunction as being of many varieties including oral medications, vacuum pumps, vascular surgery, penile prostheses, and intracavernosal injections. Both articles suggest that there is clearly a need for additional improvement in the methods employed to cause and maintain an erection since none of the current methods or devices resolve the problem adequately.

Accordingly, there is a need for a device for and method of creating and maintaining a rigid erection that overcomes the drawbacks of the known devices and methods.

OBJECTS AND SUMMARY OF THE INVENTION

It is an object of the present invention to provide an erection device, which overcomes the drawbacks of the known devices.

It is still another object of the present invention to provide an erection device, which does not painfully impinge against the penis, or pull on pubic hairs.

It is still another object of the present invention to provide an erection device, which allows for easy removal when the erection is no longer desired.

It is another object of the present invention to provide an erection device, which allows the user to adjust the amount of pressure the erection device applies to the penis.

It is still a further object of the present invention to provide an erection device, which allows the user to selectively adjust the placement of the device along the length of the penis.

It is another object of the present invention to provide an erection device, which is relatively inexpensive to manufacture and easy to use.

It is another object of the present invention to provide a method for creating and maintaining an erection which overcomes the drawbacks of the known methods.

It is still a further object of the present invention to provide a method for creating and maintaining a penile erection that is easy to utilize.

It is still a further object of the present invention to provide a device for creating an erection, which allows for nearly unlimited repetition of erection creation almost immediately after the preceding erection has been released, without damage to the penis or inflicting any pain.

The present invention includes a device and a method for creating and maintaining a rigid erection of a penis. The device having a body kept at a substantially non-contracting width and being adapted for disposition around a penis and having first and second terminals attaching to the body and being adapted for wrapping around the penis and interlocking with each other for creating and maintaining a rigid erection, and to prevent blood from exiting the penis.

BRIEF DESCRIPTION OF THE DRAWINGS

FIG. 1 is a perspective view of an erection device according to my present invention;

FIG. 2 is an enlarged cross sectional view of the erection device taken along line 2—2 of FIG. 1;

FIG. 8 is a perspective view of an alternative embodiment of the erection device according to my present invention.

DETAILED DESCRIPTION OF THE INVENTION

FIGS. 1 and 2

Figure 3:
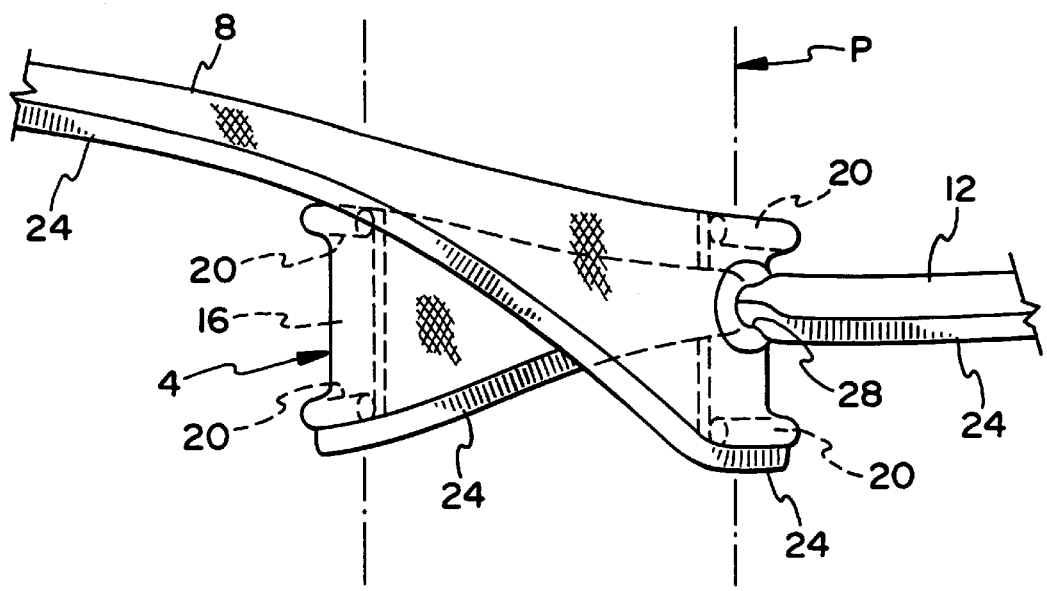
FIG. 3 is a view of the erection device of FIG. 1 in its initial stage of being placed around a penis.

An erection device made in accordance with the present invention is displayed in FIG. 1. Note, identifiers 16*a*, 16*b*, 17*a*, 17*b*, 18*a* and 18*b* relate to an alternative embodiment, as will be discussed below.

The erection device includes a body or band 4, a first terminal or end 8, a second terminal or end 12 and a member 16. Ribs or guides 20 are attached along the length of member 16. A surge sewn edge or restraining member 24 is coextensive with body 4 and first and second terminals 8 and 12. Body 4 also may include at least one aperture or hole 28.

Body 4 and first and second terminals 8 and 12 are preferred to be of a stretchable fiber material, such as but not limited to spandex or spandex-like material or any equivalent so long as the material is capable of returning to its original length after being stretched much longer than that length. It is preferred to use a stretchable material so as to allow the extension of the length of body 4 and terminals 8 and 12. It is further preferred that body 4 and terminals 8 and 18 be made of a material that is smooth or soft to the touch so as to provide a more comfortable feel to the user.

Terminals 8 and 12 may be attached to body 4 in any suitable manner so that they remain engaged to body 4, when in use.

Terminals 8 and 12 are preferred to be of a narrower width than body 4. Terminals 8 and 12 may also be narrower in width at their free ends 9 and 13 respectively than where terminals 8 and 12 attach to body 4.

Member 16 may be disposed adjacent body 4. Member 16 is to be made of a flexible material. Member 16 is adapted to substantially prevent stretchable body 4 from contracting in width while body 4 is being stretched in length, as will be discussed further below.

Member 16 may be of a non-stretchable material that is flexible or a stretchable material that is flexible, so long as it substantially aids in keeping body 4 from contracting in width while being stretched in length. Having body 4 with a substantially non-contracting width will allow disbursement over the width of body 4 any impinging forces created by the successive tightening, wrapping, and interconnecting of terminals 8 and 12, rather than having the forces acting upon a narrow area of the penis. This will be discussed further below.

As shown in FIGS. 1–5, body 4 and terminals 8 and 12 may be made from one single piece of appropriately shaped stretchable material that is folded in half along a fold edge 30, with the free edges 29 sewn together in three separate stages to form surge sewn edge or restraining member 24.

The preferred embodiment of my present invention is for member 16 to be disposed within the folded over body 4, as is readily apparent from FIGS. 1 and 2. In other words, member 16 is placed within body 4 after body 4 and one of the terminals 8 or 12 have been sewn to form a portion of surge sewn edge 24. After member 16 is placed within body 4, the other terminal 8 or 12 is then sewn to form the rest of surge sewn edge 24. Member 16 is contained within the folded over body 4 by the surge sewn edge 24 and terminals 8 and 12 since they are narrower in width than body 4.

Member 16 and body 4 may each be provided with an aperture 28. Aperture 28 in member 16 and body 4 may have a common alignment.

More than one aperture 28 in each member 16 and body 4 may be provided, and it is possible for neither to have an aperture 28. To attach member 16 to body 4, an eyelet disposed in aperture 28 may be used, as shown in FIGS. 1–5.

However, to provide further comfort and avoid any possible pinching of skin, it is preferred that aperture 28 of both member 16 and body 4 be sewn around their inner periphery or edge and thus connect member 16 to body 4.

At least two ribs or guides 20 are provided along the length of member 16. It is preferred that ribs 20 be attached coextensively with the length of member 16. It is also preferred that one rib 20 be attached to each long edge of member 16 for containment of terminals 8 and 12 when they are wrapped around a penis P, as will be discussed below. Ribs 20 are preferred to be made of, but not limited to, braided nylon. Ribs 20 are preferred to be sewn to member 16.

Surge sewn edge or member 24 is provided to allow precise adjustments to the tightness of my erection device, as will be discussed further below. Surge sewn edge 24 may be made with numerous sewing techniques such as using a sewing machine that utilizes three or four spools of thread to ultimately form a sewn edge, or the like, so long as it provides friction, restraining or interlocking forces between terminals 8 and 12 when terminals 8 and 12 are interconnected, as will be discussed further below.

Operation

FIGS. 3–5

In order to create an erection, the blood entering a penis must be restricted from returning to a user's heart. By restricting the blood from returning to the heart, the penis will become engorged and thus an erection will be created.

In order to prevent the blood from exiting a flaccid penis P, my erection device may be placed about penis P with the ribs 20 directed outward away from the penis. An appropriate terminal 8 or 12 opposite to aperture 28 is placed through aperture 28. Shown in FIG. 3 is terminal 12 passing through aperture 28. FIG. 3 shows one aperture 28 with one eyelet. Also, FIGS. 3–5 shows body 4 with only one aperture 28, as opposed to two (2) apertures 28.

With the arrangement shown in FIG. 3, terminals 8 and 12 are pulled or stretched to tighten body 4 to penis P.

Figure 4:
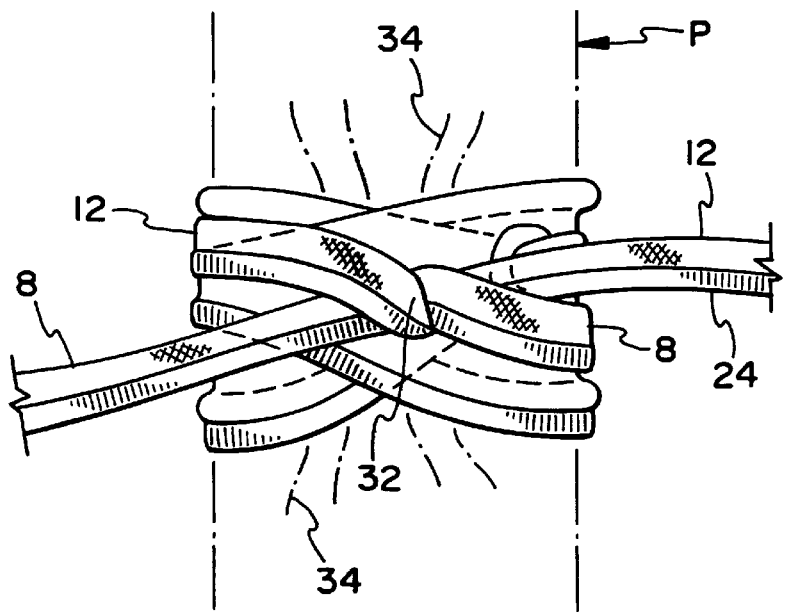
FIG. 4 is a view of the erection device of FIG. 1 having been placed around the penis with its terminal ends wrapped once around the penis and interlocked with each other.
Figures 5, 6, 7:
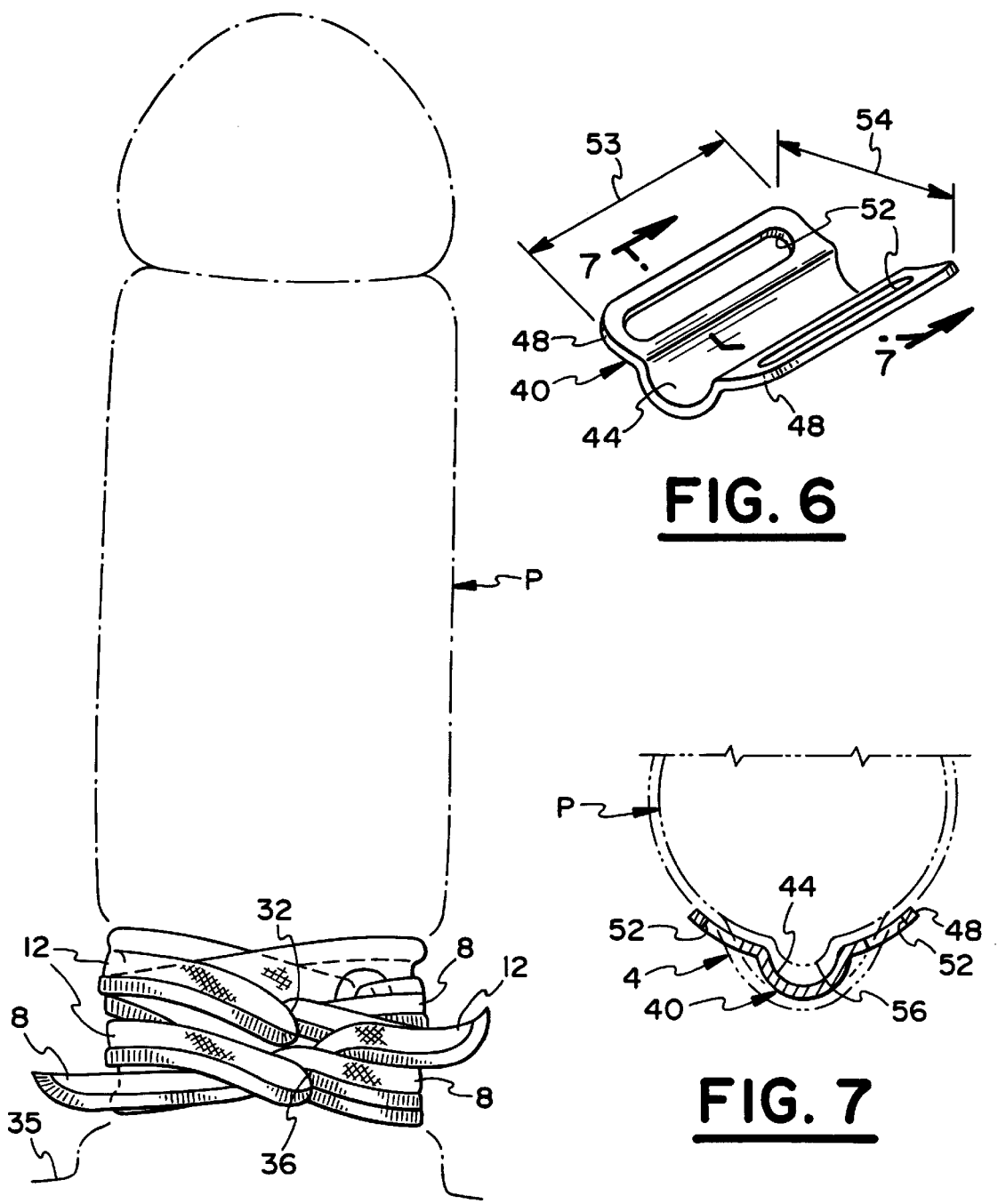
FIG. 5 is a view of the erection device of FIG. 1 shown having been placed around the penis with the terminal ends twice wrapped around the penis and interconnected with each other.
FIG. 6 is a perspective view of the urethra member according to my present invention.
FIG. 7 is a cross sectional view of the urethra device taken along the line 7—7 of FIG. 6, with the body of the erection device and the penis shown in phantom lines.

Terminals 8 and 12 are then wrapped around penis P, as shown in FIG. 4. Terminals 8 and 12 are adapted to form first interconnection 32. First interconnection 32 is preferred to be a simple overhand knot, although interconnection 32 may also be any other type of knot or any fasteners which may suitably interconnect terminals 8 and 12. It is also preferred that terminals 8 and 12 be adapted to form a second interconnection on the opposite side of penis P, from the side shown in FIG. 4. These second interconnection, not shown, is preferred to be made prior to first interconnection 32.

Terminals 8 and 12 when wrapping around penis P are kept or contained within the width of member 16 by ribs 20.

Wrinkles 34 in the skin of penis P will typically begin to develop near interconnection 32. For comfort, wrinkles 34 should and can be smoothly adjusted around penis P after the first and second interconnections, so they are not painfully located in a concentrated area, which would otherwise be the case.

With the arrangement as shown in FIG. 4, the terminals must not be adjusted too tight, so as to allow blood to flow into penis P and thus engorge it. Time is of the essence between all successive tightening.

The location or positioning of my erection device may vary along the length of the penis P. In FIGS. 3 and 4, the erection device is initially preferred to be somewhere near the middle of the full length along the shaft of penis P, and not at base 35 (shown in FIG. 5) of penis P.

As penis P begins to engorge, my erection device should be thereafter manually intermittently moved toward and finally as near as possible to base 35 of penis P as the loose foreskin of the penis p will allow. Base 35 is where penis P attaches to the user. Terminals 8 and 12 are again wrapped around penis P and are carefully tightened to form a third interconnection 36. Third interconnection 36 is also preferred to be a simple overhand knot. It is further preferred that terminals 8 and 12 be adapted to form a fourth interconnection on the opposite side of penis P, from the side shown in FIG. 5. The fourth interconnection, not shown, is preferred to be made prior to third interconnection 36.

It is preferred that as many wrappings and tightenings of interconnections or overhand knots be provided as the length of terminals 8 and 12 will allow or the user desires. All interconnections made by the user, including first, second, third and fourth interconnections and all interconnections made thereafter, are preferred to be a simple overhand knot, although all interconnections may also be any type of suitable interlocking fasteners.

Penis P will lengthen and engorge itself due to the tight wraps and interconnecting of terminals 8 and 12 around penis P, but never fully tightening the first and second interconnections. With the erection device fully tightened about penis P and located as close as possible to base 35 of penis P, penis P will become rigid and erect.

This erection may be maintained for approximately 30 minutes before the blood in penis P becomes so cold that the blood must be released to allow it to flow back to the heart for warming. However, my erection device may almost immediately be put back into place and another erection can be created for an additional approximate 30 minutes. After such time, the blood must again be released before the blood becomes too cold. This process may be repeated as many times as desired without damage to penis P or inflicting any pain at any time.

An alternative embodiment of my present invention concerns member 16. In particular, member 16 can be divided to form two (2) pieces 16a and 16b, as shown in FIG. 8. Pieces 16a and 16b abut one another within body 4 where the erection device is not in use. Pieces 16a and 16b being provided with an aperture 28. Each piece 16a and 16b being fastened or attached to body 4 by sewing around the inner periphery of aperture 28, or via an eyelet through aperture 28. Pieces 16a and 16b can also be attached by sewing through body 4 and pieces 16a and 16b near aperture 28. Pieces 16a and 16b have guides 20 sewn along their lengths, just as disclosed above for member 16.

Having member 16 made of two flexible pieces, 16a and 16b, will allow each piece 16a and 16b to be pulled around the flaccid penis by terminals 8 and 12 nearly allowing the outer ends 17a and 17b, of pieces 16a and 16b respectively, to come together when one of terminals 8 or 12 is pulled through an aperture 28 at the opposite end of the erection device.

There will be stretching of body 4 as terminals 8 and 12 are pulled with the result that the stretched portion of body 4 between the inner ends 18a and 18b, of pieces 16a and 16b respectively will have nothing to keep its width from becoming narrower.

However, that narrowing will not be too great and the successive wrappings of the terminals 8 and 12 will stay within the confines of guides 20 of pieces 16a and 16b, which have been pulled away from each other.

Having member 16 comprised of two (2) separate pieces 16a and 16b will allow the erection device to perfectly fit any man's penis regardless of its diameter.
FIGS. 6 and 7

Another embodiment of my erection device includes the use of a urethra member 40.

My erection device without the use of urethra member 40 allows a user to have an erection and orgasm, but not a "normal" ejaculation of semen, other than minor seepage. Utilizing urethra member 40 will accommodate users who desire normal ejaculation as well as an orgasm.

As shown in FIG. 6, Urethra member 40 includes channel 44 and preferably at least two flanges 48 having slits 52 therein. Channel 44 is disposed between flanges 48. Urethra Member 40 also has an inherent width 53 and length 54. The dimension of width 53 should be slightly longer than the width of body 4 to allow body 4 to pass through slits 52, as will be discussed further. Length 54 is to be narrow in relation to the total circumference of penis P so that terminals 8 and 12 when wrapped around penis P impinge the maximum amount of flesh, to reduce the flow of blood from numerous surface veins back to the user's heart. When urethra member 40 is used it will be positioned on the under side of penis P. Note, the arrangement shown in FIG. 3 is on the upper side of penis P.

FIG. 7 displays urethra device 40 in positional relationship to penis P and body 4. Urethra member 40 is disposed of the underside of penis P to allow the male urethra canal 56 to be aligned along and within u-shape channel 44. Urethra canal 56 is a conduit, which carries semen and urine through penis P. With urethra canal 56 within channel 44, semen can flow freely and thus allow ejaculation.

Urethra member 40 may be of any material so long as it provides a way for semen to flow through urethra 56. Additionally, channel 44 is preferred to be generally of a "U"-shape.

Body 4 is threaded or disposed through slit 52 of flange 48 on one side of urethra member 40, under channel 44 and through slit 52 of the other opposite flange 48. Body 4 and terminals 8 and 12 are then attached and/or tightened to penis P as disclosed above.

Use of urethra member 40 is optional to the user.

My present invention provides an erection device which is nonabrasive to the surface of penis P. Additionally, member 16, which is designed to prevent the width of body 4 from narrowing as it is tightened about penis P, provides a wide surface area on penis P around which the wraps of terminals 8 and 12 made when the erection device is positioned near base 35 may be made as tight as needed so as to cause and maintain an erection without pain being inflicted upon the user. It is to be understood that member 16 is resilient enough so that many wrappings of terminals 8 and 12 will easily impinge themselves against the flesh of penis P in order to shut down the flow of blood back to the heart.

My present invention also allows the user to selectively place body 4 along the length of penis P where it will best cause the beginning of an erection for that particular user.

My present invention will also allow the user to move the erection device closer to base 35 of penis P without entangling it in pubic hairs, while also allowing more wraps and overhand knots of terminals 8 and 12 without further tightening of the initial wraps and interconnections of surge sewn edge 24 or terminals 8 and 12 produced before said movement.

Additionally, my present invention does not entangle any pubic hair or pinch any tender skin because of the maintained width of body 4 and because it is initially placed on the loose foreskin of a flaccid penis some distance from where pubic hair is found on the penis, prior to moving it toward the base 35 of penis P.

Another advantage of my invention is that as many wrappings and knots of terminals 8 and 12 may be provided around penis P as desired by the user. The wraps of terminals 8 and 12 should be closely positioned side by side so that many blood vessels on or near the surface area of penis P under member 16 are more fully closed off.

Another advantage of my invention is that it may be simply removed after intercourse by successively untying the many interconnections which the user provided and slipping the invention off penis P with absolutely no discomfort.

Additionally, my invention is eventful to use so that the wife of the user may be fully involved in the creation of the erection.

While this invention has been described as having a preferred design, it is understood that it is capable of further modification, uses and/or adaptions following in general the principal of the invention and including such departures from the present disclosure as come within known or customary practice in the art to which the invention pertains, and as may be applied to the essential features set forth, and fall within the scope of the invention or the limits of the appended claims.

I claim:

1. A device for creating and maintaining a rigid erection of a penis, comprising:
   a) a body having a length and a width, said width being substantially non-contracting when a force is applied along said length thereof, and said body being configured for disposition around the penis; and,
   b) first and second terminals attaching to said body and being adapted for wrapping around the penis and interconnecting with each other.

2. A device as recited in claim 1, wherein:
   a) said terminals are a stretchable material.

3. A device as recited in claim 1, wherein:
   a) said body is a stretchable material.

4. A device as recited in claim 1, wherein:
   a) said terminals have a length; and,
   b) a retaining member disposed on and coextensive with said length of said terminals.

5. A device as recited in claim 1, wherein:
   a) said body has at least one aperture configured for one of said terminals to pass through for an initial wrap of said terminals around the penis.

6. A device as recited in claim 5, further including:
   a) an eyelet being disposed through said aperture.

7. A device as recited in claim 1, wherein:
   a) said terminals each having a tapered free end.

8. A device as recited in claim 1, wherein:
   a) a urethra member is provided having a channel and at least two flanges with slits therein, and said channel is disposed between said flanges;
   b) said urethra member is adapted to be disposed along the urethra canal of the penis, and for the urethral canal to be aligned with and substantially disposed within said channel; and,
   c) said body is laced through said slit of one said flange, around said channel and through the other said slit.

9. A device for creating and maintaining a rigid erection of a penis, comprising:
   a) a band having a width and being adapted for disposition around the penis;
   b) first and second ends being attached to said band and being adapted for multiple wrappings around the penis and for interconnecting with each other; and,
   c) a member being disposed adjacent said band for substantially preventing said width of said band from contracting when said ends are interconnected.

10. A device as recited in claim 9, wherein:
    a) said band has at least one aperture; and,
    b) said member has a least one aperture aligned with said at least one aperture of said band.

11. A device as recited in claim 10, wherein:
    a) said at least one aperture of said band and said member each has an inner periphery; and,
    b) said inner peripheries are sewn for connecting said member to said band.

12. A device as recited in claim 10, further including:
    a) an eyelet disposed through said aperture of said band and said member for connecting said member to said band.

13. A device as recited in claim 9, further including:
    a) a plurality of guides disposed on said member.

14. A device as recited in claim 13, wherein:
    a) said plurality of guides are substantially coextensive with said member.

15. A device as recited in claim 13, wherein:
    a) said member has two elongated edges; and,
    a) said plurality of guides includes two guides, with one of said two guides disposed substantially along one of said elongated edges of said member and the other of said two guides disposed substantially along the other of said elongated edges of said member.

16. A device as recited in claim 9, wherein:
    a) first and seconds ends are stretchable; and
    b) said band is a stretchable material.

17. A device as recited in claim 9, wherein:
    a) said member is flexible.

18. A device as recited in claim 9, wherein:
    a) said first and second ends have a length; and,
    b) a surge sewn edge disposed on and coextensive with said first and second ends and said band.

19. A device as recited in claim 9, wherein:
    a) a urethra member having a channel and at least two flanges with slits therein, said channel disposed between said flanges;
    b) said urethra member adapted to be disposed along the penis allowing urethra canal of the penis to be aligned with and within said channel; and,
    c) said first end or said second end being laced through said slit of one said flange, around said channel and through said slit of other said flange.

20. A device as recited in claim 9, wherein:
    a) said member is at least two separate pieces each having an inner end, said pieces configured with said inner ends abutting when said terminals are not interconnected and to have said inner ends non-adjacent when said terminals are interconnected.

21. A method of creating and sustaining a rigid erection of a penis, comprising the steps of:
    a) supplying a body having terminals a length and a width, said width being substantially non-contracting when a force is applied along said length thereof,
    b) placing said body about the penis;
    c) wrapping said terminals at least once around the penis; and,
    d) interconnecting said terminals to prevent blood within the penis from exiting.

22. A method as recited in claim 21, further comprising:
    a) providing a urethra member having a channel and at least two flanges with slits therein, with said channel disposed between said flanges;
    b) placing said urethra member beneath the penis with a urethra canal of the penis aligned with said channel;
    c) threading said terminal through said slit of one of said flanges around said channel and through said slit of other said flange.

23. A method as recited in claim 21, wherein:
    a) said interconnection step is making at least one overhand knot per wrapping of said terminals.

* * * * *